(12) United States Patent
Harvat

(10) Patent No.: US 8,308,668 B1
(45) Date of Patent: Nov. 13, 2012

(54) SCAPULOTHORACIC INTERFACE MEDICAL DEVICE

(76) Inventor: Donna Marie Harvat, Marysville, PA (US)

( * ) Notice: Subject to any disclaimer, the term of this patent is extended or adjusted under 35 U.S.C. 154(b) by 855 days.

(21) Appl. No.: 12/429,271

(22) Filed: Apr. 24, 2009

(51) Int. Cl.
*A61H 7/00* (2006.01)
*A61F 5/00* (2006.01)
(52) U.S. Cl. .................. 601/134; 601/135; 606/237
(58) Field of Classification Search .......... 601/134–135, 601/136–137, 23; 606/237; 600/306, 340
See application file for complete search history.

(56) References Cited

U.S. PATENT DOCUMENTS

| D262,908 S | * | 2/1982 | Pesco ............................. D24/36 |
| 4,483,328 A | | 11/1984 | Wolocko |
| 5,368,589 A | | 11/1994 | Tovey et al. |
| 6,159,169 A | * | 12/2000 | Lambden ......................... 601/15 |
| 7,361,153 B1 | | 4/2008 | Martin |
| 2006/0247563 A1 | | 11/2006 | Martin et al. |
| 2006/0293619 A1 | | 12/2006 | Louis |
| 2007/0191745 A1 | | 8/2007 | Tucker |
| 2009/0240177 A1 | * | 9/2009 | Sullivan ......................... 601/136 |

OTHER PUBLICATIONS

Patterson Medical Products, Inc., 2007 Professional Rehab Catalog, 2007, pp. 640-641 (showing various goniometers), USA.

* cited by examiner

*Primary Examiner* — Kevin C Sirmons
*Assistant Examiner* — Ophelia A Hawthorne
(74) *Attorney, Agent, or Firm* — Hooker & Habib, P.C.

(57) ABSTRACT

The invention relates to a medical device and method for evaluating and treating scapulothoracic mobility disorders. The invention facilities examination and treatment of the scapulothoracic motion interface.

21 Claims, 6 Drawing Sheets

SCAPULOTHORACIC INTERFACE MEDICAL DEVICE

FIELD OF THE INVENTION

The invention relates to a medical device and method for evaluating and treating scapulothoracic mobility disorders.

BACKGROUND OF THE INVENTION

Healthy shoulder movement depends the scapulothoracic interface. The scapulothoracic motion interface is the site of movement between the scapula (shoulder blade) and the rear chest wall (thoracic cavity or ribcage). In normal motion, the scapula moves across the rear chest wall by gliding on the scapulothoracic interface.

Tight body tissues located at the interface between the scapula and rear chest wall limit scapulothoracic mobility, thus limiting shoulder movement and contributing to upper extremity pain. Conventional therapy for relieving tightness involves a therapist manipulating these tissues by extending their fingers underneath and between the scapula and ribcage. This requires exerting force on the tissues and scapula during which the small bones of the therapist's hands are placed under stress and may tire quickly or become injured.

The therapist subjectively evaluates the seriousness of the tissue tightness by-feel from mild to moderate to severe and lacks a method to objectively measure scapulothoracic interface tightness and the effectiveness of treatments.

Another problem with the scapulothoracic interface is scapular winging. Scapular winging is the result of weak or injured muscles between the scapula and rear chest wall so that the scapula rises away from the chest wall. Scapular winging can also limit scapulothoracic mobility and related shoulder movement.

Scapular winging is subjectively evaluated by visual inspection from "mild" to "moderate" to "severe". Therapists lack a method to objectively measure scapular winging and the effectiveness of treatments.

Thus there is a need for a medical device for evaluating and treating scapulothoracic mobility disorders. The medical device should allow a therapist to objectively measure patient scapulothoracic tightness and scapulothoracic winging and evaluate patient condition and the effectiveness of treatment. The device should allow a therapist to exert force on scapulothoracic tissues without stressing the therapist's hands.

SUMMARY OF THE INVENTION

The invention is a medical device for evaluating and treating scapulothoracic mobility disorders. The medical device allows a therapist to objectively measure a patient's scapulothoracic tissue tightness and scapulothoracic winging to evaluate patient condition and the effectiveness of treatment. The device allows a therapist to exert force on tissues at the scapulothoracic interface without stressing the therapist's hands.

The medical device includes a base that is placed on a patient's back and a handle for control of the device. The base includes a measurement edge that is extended under a patient's scapula. The base includes a gage that allows a therapist to measure the depth of measurement edge insertion into the recess formed between the scapula and rear chest wall. The depth of insertion provides an objective indication of scapulothoracic mobility.

In further use, the therapist can use the device to exert forces on the tissues at the scapulothoracic interface while measurement edge is inserted under the patient's scapula. The handle allows easy use by either hand and prevents stresses from being transmitted to the small bones of the hand during treatment. The handle additionally allows the therapist exert forces on the handle using two hands or a forearm. This allows the therapist to conduct longer and more concentrated treatment sessions with lowered risk of hand stress and injury.

The device may also measure scapular winging by including a second gage that measures the distance of vertical separation between the scapula and the rear chest wall. The second gage objectively measures scapular winging.

Other objects and features of the invention will become apparent as the description proceeds, especially when taken in conjunction with the accompanying drawing sheets illustrating embodiments of the invention.

DETAILED DESCRIPTION OF THE INVENTION

Figure 1:
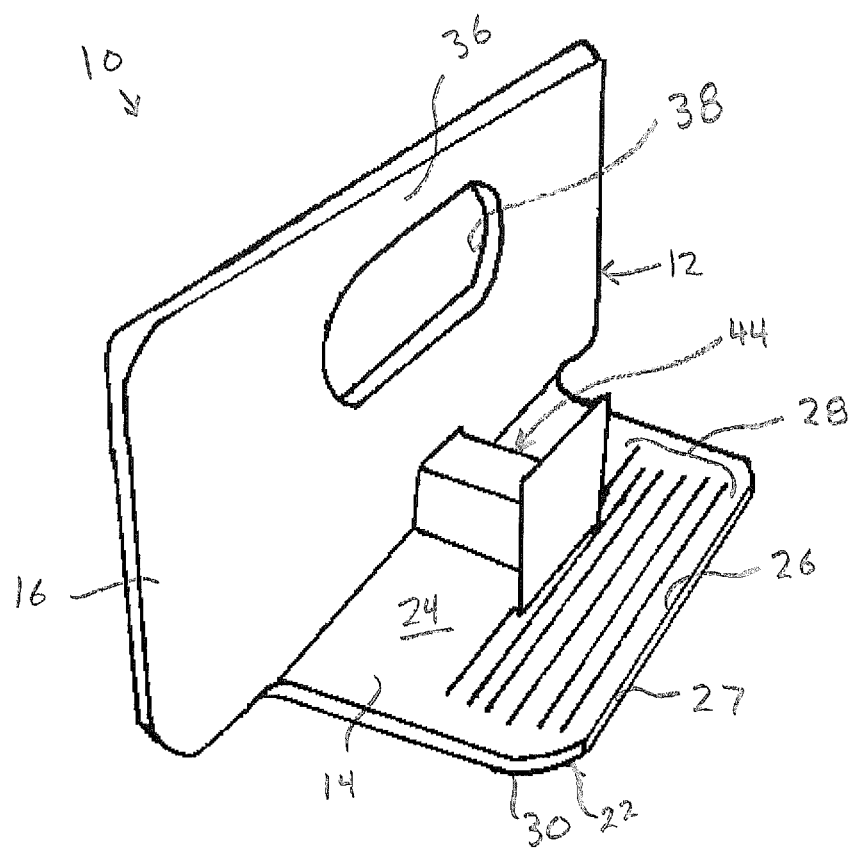
FIG. 1 is a perspective view of the device.
Figure 2:
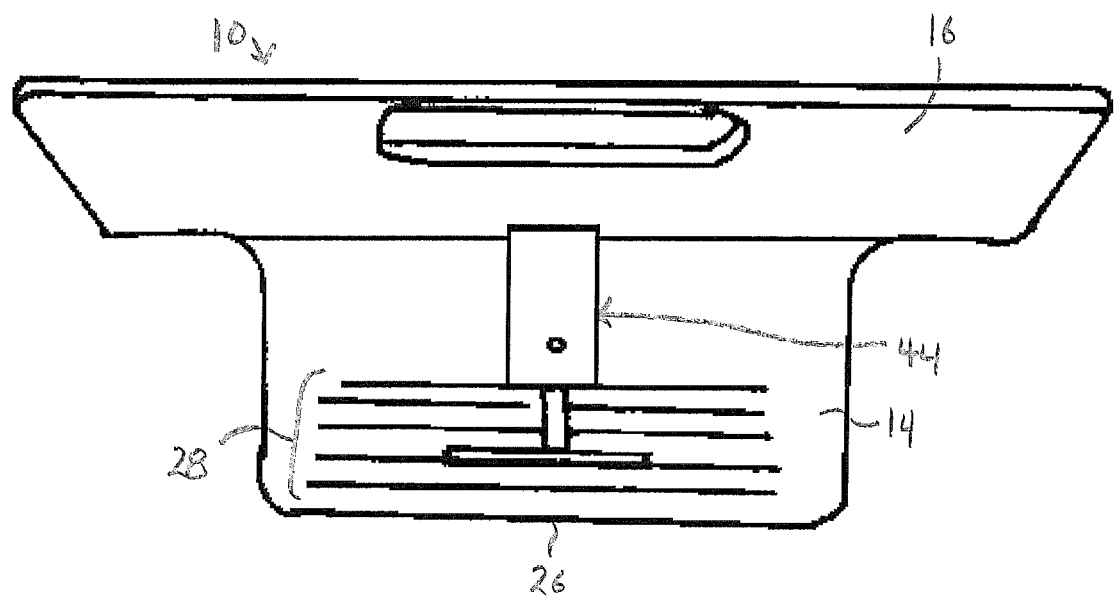
FIG. 2 is an top view of the device.

Scapulothoracic interface medical device 10 is made up of an elongate, generally L-shaped body 12 having a base 14 and a handle 16. Body 12 may be formed from plastic, such as acrylic, polycarbonate or other commonly available formable materials.

Base 14 is generally rectangular with a length 18 and a width 20 and includes bottom contact surface 22, top surface 24 and measurement edge 26. Engagement surface 27 extends from measurement edge 26 to bottom contact surface 22. The top surface 24 of base 14 includes a measurement scale 28 made up of a number of printed or etched lines parallel to measurement edge 26 and extending at regular distances from edge 26 toward handle 16. Base 14 may also include rounded corners 30.

Handle 16 is generally rectangular with a length 32 and a width 34. The handle includes a grip 36 and a handle aperture 38 to allow a therapist to use their thumb to control handle 16 as seen in FIGS. 11-15. Aperture 38 may be centrally located on the handle and symmetrically ovular or elliptical in shape to allow a therapist to use either their right or left thumb when gripping the handle. Alternatively, a therapist may grip the handle with two hands or use their forearm to transmit forces to the handle.

Handle 16 may also include contours extending along length 32 to either side of handle aperture 38 (not illustrated). The contours may be shaped to conform a therapist's hand when a right or left thumb is used to gripping to the handle.

Base 14 may have a length 18 less than handle length 32. The larger handle length 32 allows a therapist to effectively apply a concentrated force to measurement edge 26 as well as allow a therapist to use two hands or a forearm when controlling device 10 as explained in greater detail below.

Figure 3:
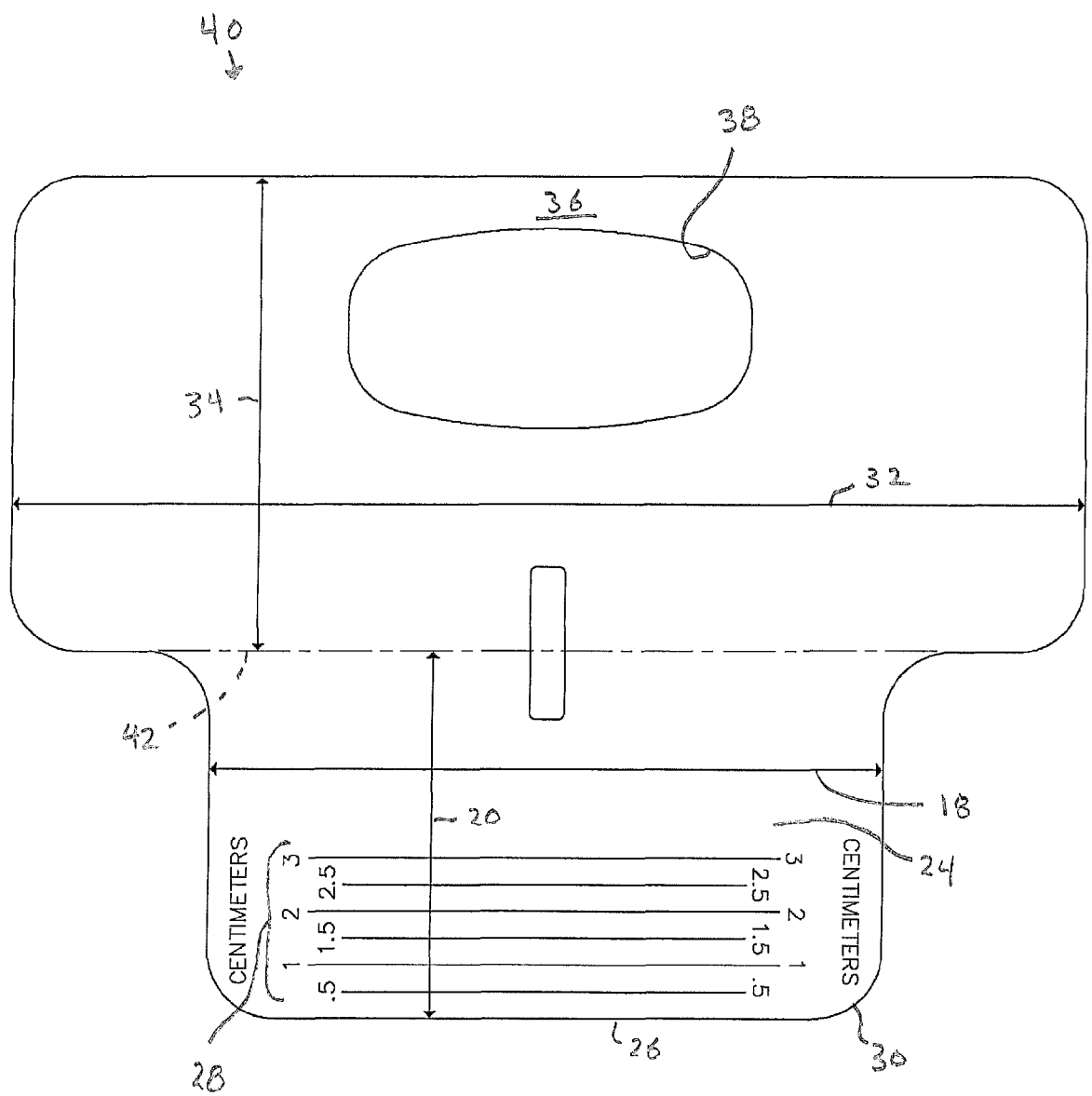
FIG. 3 is an top view for a preform for producing the device body.
Figure 4:
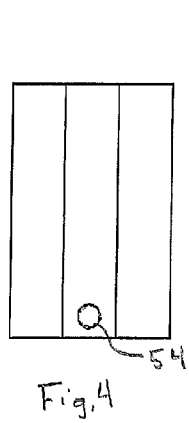
FIG. 4 is a top view of the sliding gage assembly housing.
Figure 5:
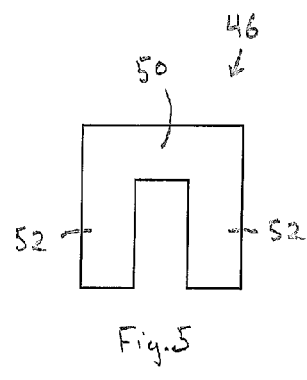
FIG. 5 is a front view of the sliding gage assembly housing.
Figure 6:
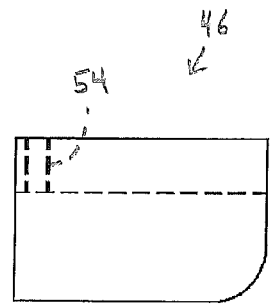
FIG. 6 is a side view of the sliding gage assembly housing.
Figure 7:
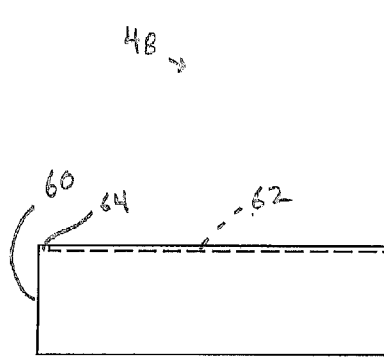
FIG. 7 is a side view of the sliding gage assembly sliding member.
Figure 8:
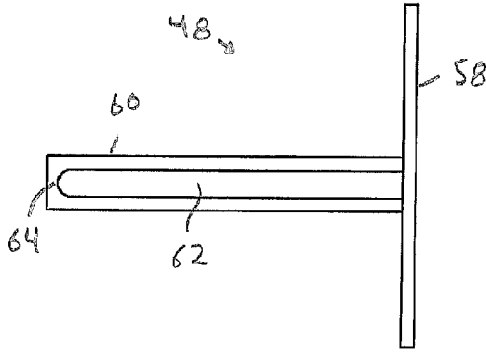
FIG. 8 is a top view of the sliding gage assembly sliding member.

Body 12 may be formed from preform 40, which is molded or cut from plastic of other materials. See FIG. 3. Preform 40 is folded or bent along line 42 to form a L-shaped body 12.

If desired, device 10 may include sliding gage assembly 44. Assembly 44 is made up of housing 46 and sliding member 48. Housing 46 is formed from base 50 and two legs 52 extending away from base 50 and generally parallel to each other to form a generally U-shaped housing. Fastener aperture 54 extends though base 50 at one end of the housing. Housing 46 is joined to body 12 at the intersection of base 14 and handle 16 so that base 14, base top surface 24 and legs 40 form passage 56.

Sliding member 48 is made up of a plate 58 attached to elongate beam 60 so that the bottoms of the plate and beam are aligned and the beam is substantially perpendicular to the length of the plate. Groove 62 is located on the upward facing portion of beam 62. Groove 62 extends from the end of the beam attached to the plate to a stop 64 located at the other end of the beam.

Sliding gage assembly 44 is formed by inserting the free end of beam 60 into passage 56. Sliding member 48 is held in place by inserting a fastener 66 though fastener aperture 54 so that the lower end of fastener 66 extends into groove 62. Stop 64 prevents sliding member 48 from becoming detached form assembly 44 while fastener 66 is in place.

Figure 9:
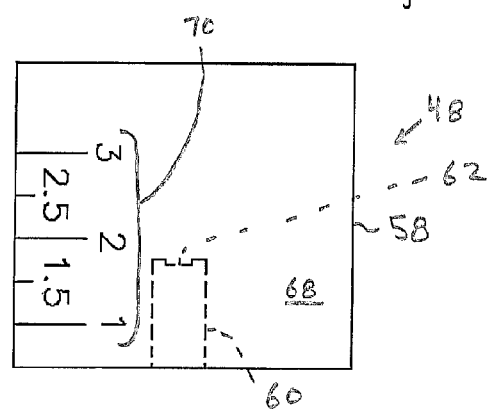
FIG. 9 is a front view of the sliding gage assembly sliding member.
Figure 10:
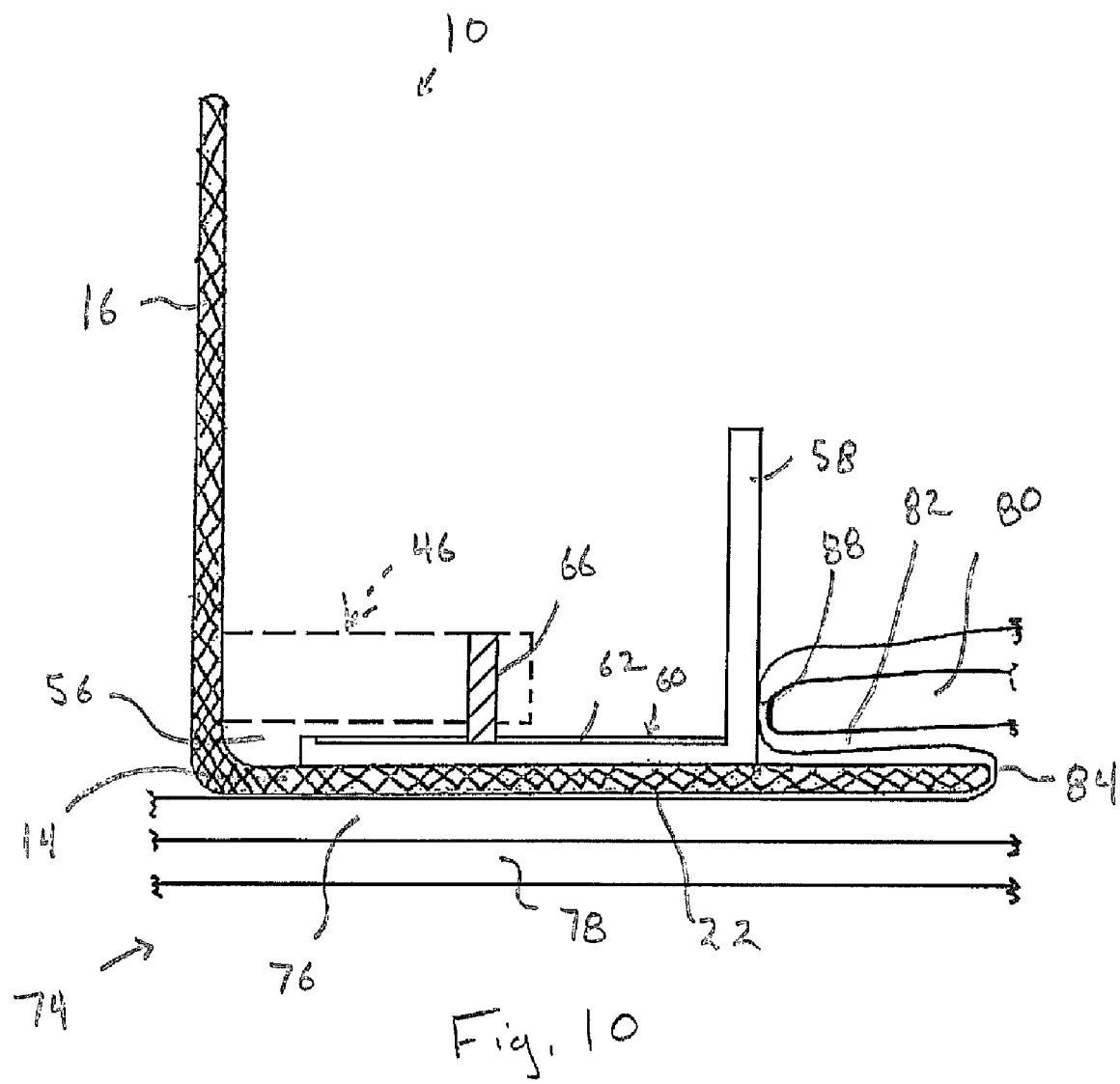
FIG. 10 is a cutaway side view of the device in use on a patient.

If desired, the front face 68 of plate 58 may include a second measurement scale 70 like scale 28 made up of a number of printed or etched lines as shown in FIG. 9.

Housing 46 and sliding member 48 may be formed from the same material as body 12.

In use, device 10 is placed on a patient's back 74 so that contact surface 22 rests on the layer of soft thoracic tissues 76 located above the patient's rib cage 78. Scapula 80 is surrounded by soft scapular tissue 82. Back tissue 76 and scapular tissue 82 join at scapulothoracic interface 84.

To evaluate scapulothoracic mobility for a shoulder, a therapist places base 14 along the patient's back so that contact surface 22 is in contact with the back and measurement edge 28 is placed adjacent scapula 80. Base 14 is then gently slid underneath scapula 80. Flat contact surface 22 and rounded corners 30 facilitate sliding base 14 underneath scapula 80.

As base 14 is slid underneath scapula 80, the base forms a recess 86 between the scapula and the rear chest and engagement surface 27 establishes contact with the soft tissue at scapulothoracic interface 84. When surface 27 meets resistance from the soft tissue at scapulothoracic interface 84, the therapist stops sliding base 14 under scapula 80.

Figure 11:
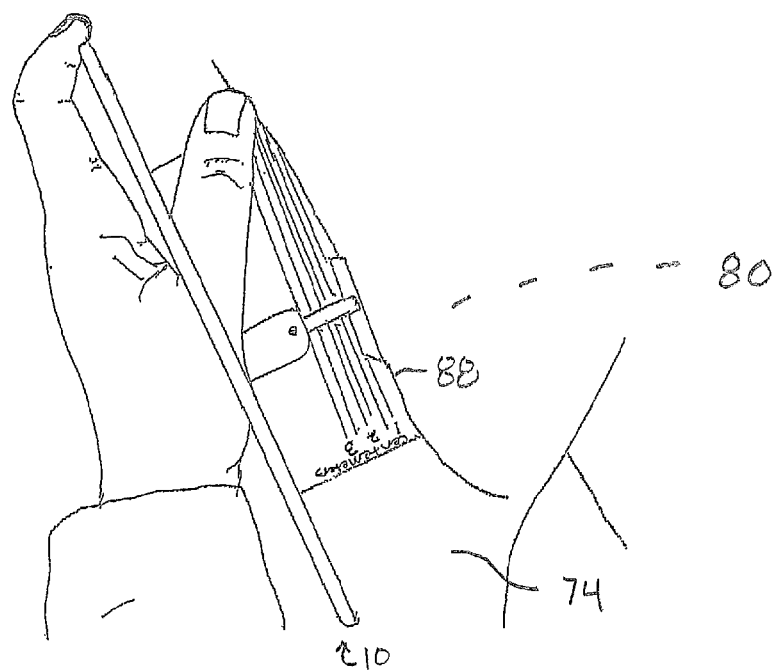
FIG. 11 is a top view of the device in use on a patient.
Figure 12:
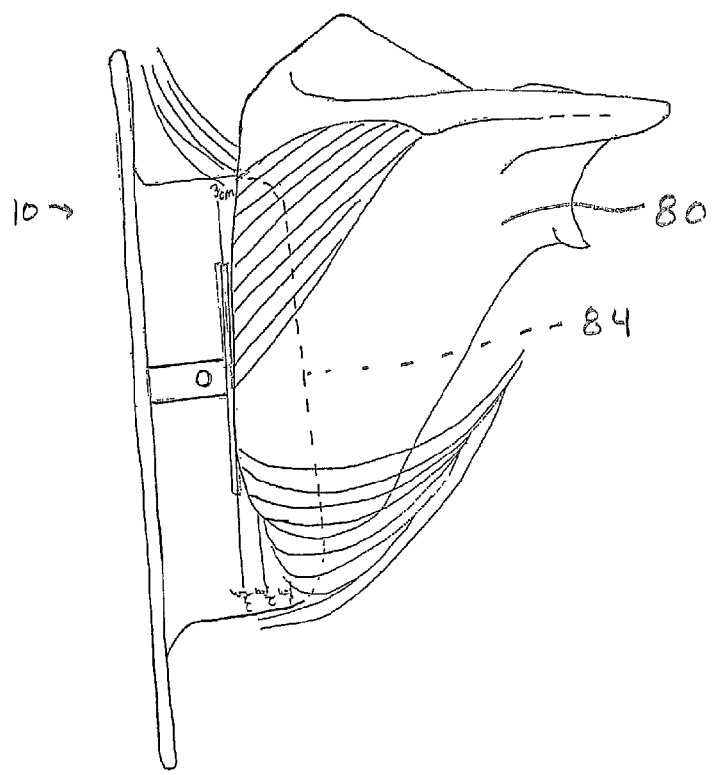
FIG. 12 is a top view of the device in use with patient skin removed.
Figure 13:
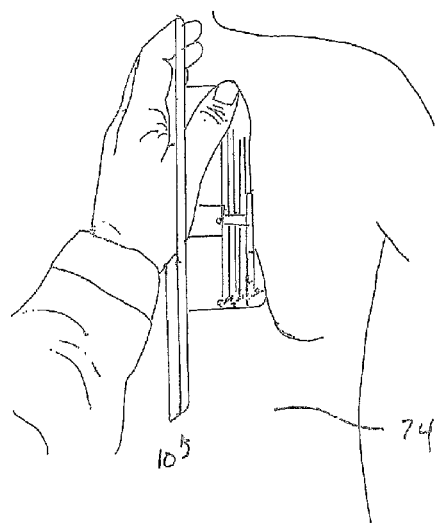
FIG. 13 is a top view of the device in use on a patient.

The therapist then measures the location of outer scapula edge 88 on measurement scale 26 as shown in FIGS. 11 through 13. Sliding gage assembly 44 may be used with measurement scale 28 to measure the distance between scapulothoracic interface 84 and scapula edge 88. The distance is noted by the therapist as an objective indication of the tightness of soft tissue at the scapulothoracic interface.

The therapist may then continue to use the device to treat the soft tissues at the scapulothoracic interface. Treatment is applied by the therapist exerting pressure on the scapulothoracic tissues. The pressure encourages loosening of the tissues. This loosening increases mobility between the scapula and the rear chest wall.

Figure 14:
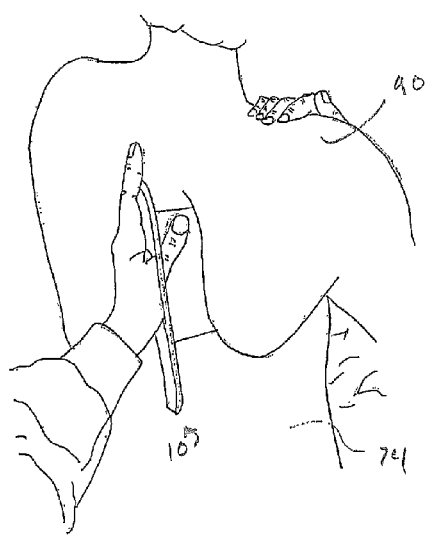
FIG. 14 shows the device prepared to manipulate a patient's scapula.
Figure 15:
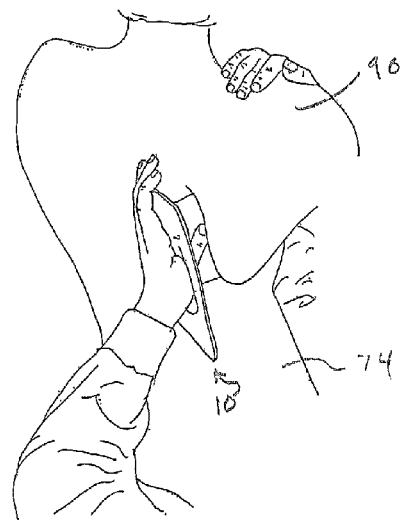
FIG. 15 shows the device used to manipulate a patient's scapula.

The therapist may grasp the patient's shoulder 90 as shown in FIG. 14 and turn it slightly upward as shown in FIG. 15. As the shoulder is turned, the therapist allows base 14 to more fully apply pressure from engagement surface 27 to the soft tissues at scapulothoracic interface 84. Pressure is maintained until the therapist determines that a loosening effect upon the soft tissues has been achieved.

Device 10 may be held by handle 16 by one hand as shown in FIGS. 14 and 15. Alternatively, the therapist may choose to place a forearm against handle 16 or use two hands on the handle in order to exert a greater force against the soft tissues at scapulothoracic interface 84. The handle allows easy use by one hand, two hands or by the therapist's forearm. A handle having a grip 36 larger area than engagement surface 27 base allow the therapist to apply concentrated forces to the soft tissues at scapulothoracic interface 84 without exposing their hands to undue pressures.

To evaluate scapular winging, the therapist places base 14 along the patient's back 74 so that contact surface 22 is in contact with the back and measurement edge 28 is placed adjacent scapula 80. Base 14 is placed adjacent scapula 80. The therapist then measures the position of edge 80 on second measurement scale 70. The reading on measures the winging distance between scapula edge 88 and the back 74. The distance is noted by the therapist as an objective indication of the weakened or damaged muscles at the scapulothoracic interface.

Alternatively, scapular winging may be measured by placing device 10 on the patient's back 74 so that base 14 is placed generally perpendicular to the back and measurement edge 26 is in contact with back 74. The therapist may then measure the position of edge 80 on measurement scale 28.

While I have illustrated and described preferred embodiments of my invention, it is understood that there are capable of modification, and I therefore do not wish to be limited to the precise details set forth, but desire to avail myself of such changes and alterations as fall within purview of the following claims.

I claim:

1. A device for evaluating and treating scapulothoracic mobility disorders between a patient's scapula and rear chest wall, the device comprising a generally elongate body; the body comprising a generally flat base and a generally flat handle extending away from the base, the generally flat base comprising a base width and a base length extending across the generally flat base the base extending to a measurement edge, the base length perpendicular to the base width, a generally flat contact surface between the measurement edge and the handle and the contact surface facing away from the handle, the contact surface generally parallel to the generally flat base, and a measurement scale visible on the side of the base adjacent the generally flat handle, the measurement scale extending from the base measurement edge toward the generally flat handle; the generally flat handle comprising a handle width and a handle length and including a grip above the base; the base adapted to fit within a recess formed between the scapula and the rear chest wall with the base on the rear chest wall and the scapula overlying the base so that the recess depth may be measured by the location of the outer edge of the scapula on the measurement scale wherein the base may be used to exert forces on body tissues located within the recess.

2. The device of claim 1 wherein the generally flat base has a generally uniform thickness.

3. The device of claim 2 wherein the generally flat base and the handle have a generally uniform thickness.

4. The device of claim 2 wherein the generally uniform thickness is approximately 0.4 centimeters.

5. The device of claim 1 wherein the handle extends away from the generally flat base at an approximately ninety degree angle and the body is generally L-shaped.

6. The device of claim 5 wherein the handle comprises a handle aperture.

7. The device of claim 1 wherein the measurement scale comprises a sliding gauge.

8. The device of claim 1 wherein the measurement edge length is approximately equal to the base length.

9. The device of claim 1 wherein the body is comprised of plastic.

10. The device of claim 1 comprising a second measurement scale extending substantially perpendicular to and away from the base.

11. A device for evaluating and treating scapulothoracic mobility disorders between a patient's scapula and rear chest wall, the device comprising:
   a generally elongate body having a generally flat base, a generally flat handle extending away from the base, the generally flat handle comprising a handle width and a handle length extending across the generally flat handle, the handle and including a grip above the base, the generally flat base having a generally uniform thickness, a base width perpendicular to a base length and a base measurement edge;
   the base comprising a generally flat contact surface and a measurement scale facing away from the contact surface and extending from the base measurement edge toward the handle and generally parallel to the contact surface;
   the base adapted to fit within a recess formed between the scapula and the rear chest wall with the base on the rear chest wall and the scapula overlying the base so that the recess depth may be measured by the location of the outer edge of the scapula on the measurement scale wherein the base may be used to exert forces on body tissues located within the recess.

12. The device of claim 11 wherein the handle extends away from the base at an approximately ninety degree angle and the body is generally L-shaped.

13. The device of claim 12 wherein the base and handle thicknesses are substantially similar.

14. The device of claim 13 wherein the thicknesses are approximately 0.4 centimeters.

15. The device of claim 11 comprising a second measurement scale extending substantially perpendicular to and away from the contact surface.

16. The device of claim 11 wherein the body is comprised of plastic.

17. The device of claim 11 wherein the measurement scale comprises a sliding gauge.

18. A method for evaluating and treating scapulothoracic mobility disorders originating at the interface between an individual's scapula and rear chest wall, the method comprising the steps of:
   (a) placing a device comprising a handle and a generally flat base, the base having a generally flat contact surface extending to an engagement surface, on the individual's rear chest wall;
   (b) inserting the engagement surface of the device into the recess formed between the individual's scapula and rear chest wall;
   (c) placing the engagement surface against the interface and the flat contact surface against the rear chest wall; and
   (d) measuring the distance between the engagement surface and the outer edge of the scapula.

19. The method of claim 18 further comprising the steps of:
   (f) exerting a force on the handle;
   (g) transferring the force from the handle to the engagement surface; and
   (h) transferring the force from the engagement surface to the interface.

20. The method of claim 19 further comprising the step of:
   (i) manipulating the individual's shoulder to simulate motion of the scapula relative to the rear chest wall.

21. The method of claim 18 further comprising the steps of:
   (e) measuring the distance between the outer edge of the scapula and the rear chest wall.

* * * * *